United States Patent
Tamirisakandala

(10) Patent No.: US 9,651,524 B2
(45) Date of Patent: May 16, 2017

(54) METHOD OF ULTRASONIC INSPECTION OF AS-CAST TITANIUM ALLOY ARTICLES

(71) Applicant: RTI International Metals, Inc., Niles, OH (US)

(72) Inventor: Sesh Tamirisakandala, Solon, OH (US)

(73) Assignee: RTI International Metals, Inc., Niles, OH (US)

(*) Notice: Subject to any disclaimer, the term of this patent is extended or adjusted under 35 U.S.C. 154(b) by 259 days.

(21) Appl. No.: 14/279,451

(22) Filed: May 16, 2014

(65) Prior Publication Data

US 2014/0352148 A1 Dec. 4, 2014

Related U.S. Application Data

(60) Provisional application No. 61/829,707, filed on May 31, 2013.

(51) Int. Cl.
*G01N 29/00* (2006.01)
*G01N 29/04* (2006.01)

(52) U.S. Cl.
CPC ...... *G01N 29/043* (2013.01); *Y10T 29/49336* (2015.01); *Y10T 29/49774* (2015.01)

(58) Field of Classification Search
CPC .................................................. G01N 29/348
See application file for complete search history.

(56) References Cited

U.S. PATENT DOCUMENTS

| | | | |
|---|---|---|---|
| 4,331,857 A | 5/1982 | Crisci et al. | |
| 4,480,475 A | 11/1984 | Tsao et al. | |
| 4,561,888 A | 12/1985 | Okuda et al. | |
| 4,968,348 A | 11/1990 | Abkowitz | |
| 5,041,262 A | 8/1991 | Gigliotti, Jr. | |
| 5,131,959 A | 7/1992 | Huang | |
| 6,332,935 B1 | 12/2001 | Gorman et al. | |
| 6,370,956 B1 | 4/2002 | Bewlay et al. | |
| 6,393,916 B1* | 5/2002 | Bewlay ............... | G01N 29/348 73/597 |

(Continued)

FOREIGN PATENT DOCUMENTS

| | | |
|---|---|---|
| EP | 1887093 | 2/2008 |
| WO | 2005060631 | 7/2005 |
| WO | WO2005060631 | 7/2005 |

OTHER PUBLICATIONS

Foister, S.A.M.; McKenzie, S.G.; Chivers, R.C., An Experimental Investigation of Ultrasonic "Grain Noise" in Titanium-6AL-4V, Review of Progress in Quantitative Nondestructive Evaluation, vol. 15, 1996, pp. 1479-1485.

(Continued)

*Primary Examiner* — Jessee Roe
(74) *Attorney, Agent, or Firm* — Greenberg Traurig, LLP

(57) ABSTRACT

A method is provided of non-destructively inspecting titanium alloy articles in the as-cast condition using ultrasonic waves to detect internal flaws, comprising modification of grain structure in the as-solidified ingot structure by the addition of trace boron to various titanium alloys. The ability to ultrasonically inspect as-cast billets combined with improved hot workability provided by trace boron enhancement permits an economical method of manufacture of titanium alloy articles destined for high performance applications.

19 Claims, 2 Drawing Sheets

(56) References Cited

U.S. PATENT DOCUMENTS

| | | |
|---|---|---|
| 6,401,537 B1 | 6/2002 | Gigliotti, Jr. et al. |
| 7,322,396 B2 | 1/2008 | Govern et al. |
| 8,128,764 B2 | 3/2012 | Miracle et al. |
| 8,206,121 B2 | 6/2012 | Rose |

OTHER PUBLICATIONS

Banchet, J.; Sicard, R.; Zellouf, D.E., and Chahbaz, A., Phased Arrays Techniques and Split Spectrum Processing for Inspection of Thick Titanium Casting Components, Review of Quantitative Nondestructive Evaluation, vol. 22, 2003, pp. 793-798.

Tamirisakandala, S., R.B. Bhat, J.S. Tiley, and D.B. Miracle. "Grain Refinement of Cast Titanium Alloys Via Trace Boron Addition", Scripta Materialia, 53, 2005, pp. 1421-1426.

\* cited by examiner

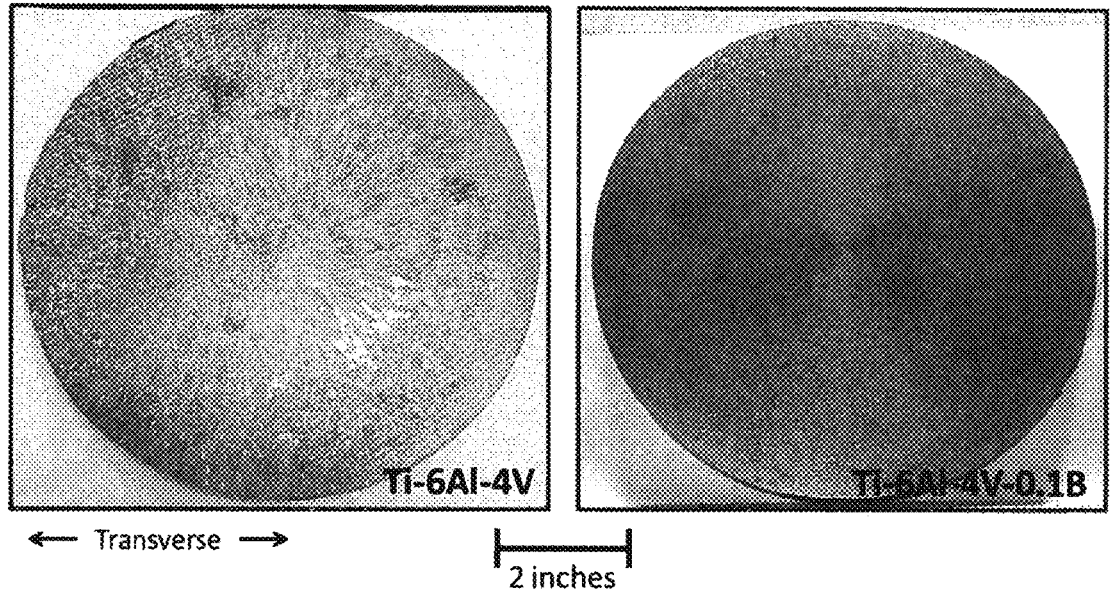
FIG-1A PRIOR ART
FIG-1C
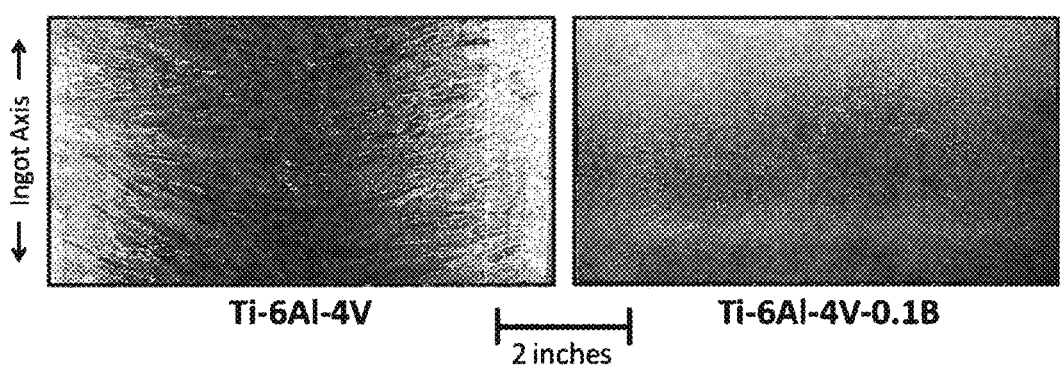
FIG-1B PRIOR ART
FIG-1D

METHOD OF ULTRASONIC INSPECTION OF AS-CAST TITANIUM ALLOY ARTICLES

CROSS REFERENCE TO RELATED APPLICATIONS

This application is a non-provisional application of U.S. Provisional Patent Application Ser. No. 61/829,707, filed May 31, 2013, the disclosure of which is incorporated herein by reference.

BACKGROUND OF THE INVENTION

1. Field of the Invention

The present invention relates to a method of ultrasonic inspection of titanium alloy articles in the as-cast condition, and more specifically the ability to detect sub-surface flaws without the need of significant processing to improve ultrasonic inspectability.

2. Description of the Prior Art

The use of titanium alloys for many critical structural applications has resulted in the development and use of a variety of inspection methods. These methods can be classified into volume methods that allow interrogation of the interior (subsurface) of the material and surface methods that permit detection of surface anomalies. These methods are complementary in nature and used concurrently to achieve a high confidence level in detecting undesired conditions that could compromise properties in the material or component. Surface defects are more common, but also are easier to detect and, therefore, catastrophic failure due to surface defects is less likely. Failures from internal defects, on the other hand, are obviously of greater concern compared to surface defects. The ability to consistently find small internal defects has improved the reliability of high performance structures and has led to reductions of unexpected service failures. The structural efficiency of these components also has increased because of the ability to design to higher operating stresses without increasing the risk of unexpected failure.

Ultrasonic inspection of titanium and titanium alloys is the most common inspection method used when the material is intended for use in high performance applications such as the aerospace and energy industries. In this inspection method, ultrasonic waves are induced in the material using a piezoelectric transducer. The transducer is coupled by water or other coupling media to the piece being inspected. The detection of subsurface defects is based on the reflection of some of the incident ultrasonic waves from regions lying along their path. This reflection occurs whenever there is a region that has different acoustic impedance or resistance to the transmission of the ultrasonic waves. During operation, the transducer sends waves, stops sending and waits to detect the reflected waves. There always is a reflection from the front and rear faces of the piece being inspected, which are useful length markers to help physically locate sources of other reflections along the ultrasonic pathway.

Ultrasonic testing typically requires that items to be detected possess high acoustic reflectance behaviors from bulk material under ultrasonic inspection. This different behavior permits the ultrasonic inspection technique to confidently detect flaws and imperfections. Materials with large, elastically anisotropic grains, such as, but not limited to, cast ingots of steels, titanium alloys and nickel alloys, are often difficult to evaluate by ultrasonic testing. The difficulties arise, at least in part, because sound waves, which are used for ultrasonic inspection, can be partially reflected from grains, and represent a background "noise." The generated background noise can mask flaws in the material, and is thus undesirable. The scattering of sound in a polycrystalline metallic material body, which is also known as attenuation of a propagating sound wave, can be described as a function of at least one of the following: grain dimensions, intrinsic material characteristics, and ultrasound frequency. Use of focused ultrasonic beams to enhance a flaw fraction within any instantaneously insonified volume of material is common. These developed ultrasonic inspection techniques can identify indications based both on maximum signal, as well as signal to noise. However, if the noise level is high, which is the case with coarse grain materials, reliable detection of internal flaws using ultrasonics is not possible.

Titanium ingots in the as-cast condition exhibit extremely coarse grains, in the range of several millimeters to centimeters. These grains follow solidification patterns and are "noisy," which implies that frequent, low amplitude reflections are observed during ultrasonic inspection. In the extreme, this noise gives rise to false positives or insufficient inspection sensitivity necessary to meet the detectability requirements. The most effective solution to this situation is to process the ingots to refine grain structure. Several steps of hot working (repeated heating and mechanical working) to refine grain structures is the standard practice to accomplish this objective. However, this processing is significantly expensive and time consuming. Intermediate products such as billets are routinely inspected ultrasonically to assess whether its quality is suitable for the final processing and eventual service. These intermediate products are products which have already undergone the above-noted hot working before the ultrasonic inspection is performed.

There is a need for an improved approach to be able to reliably inspect titanium billets in the as-cast condition. The improved approach should permit detection of internal flaws with low interference from noise, and also be compatible with subsequent processing of the billets into articles. The present invention fulfills this need, and further provides related advantages.

SUMMARY

In one aspect, the invention may provide a method comprising the steps of providing an as-cast titanium article made up of a titanium base alloy and boron in a range of about 0.05 to 0.20 percent by weight; and ultrasonically inspecting the as-cast titanium article to determine whether the article has internal flaws.

In another aspect, the invention may provide a method comprising the steps of casting a titanium ingot made up of a titanium base alloy and boron in a range of about 0.05 to 0.20 percent by weight; and ultrasonically inspecting the titanium ingot to determine whether the article has internal flaws before subjecting the ingot to any hot working.

BRIEF DESCRIPTION OF THE DRAWINGS

FIGS. 1a-1d include photographs showing a comparison of a sample of a prior art ingot and a sample ingot within the scope of the invention. In particular, FIGS. 1a and 1b are photographs respectively of a transverse section and a longitudinal section of a prior art 8-inch ingot formed of Ti-6Al-4V, illustrating the macro grain structure thereof. FIGS. 1c and 1d are photographs respectively of a transverse section and a longitudinal section of a sample 8-inch ingot formed of Ti-6Al-4V-0.1B.

DETAILED DESCRIPTION OF THE INVENTION

Figure 2:
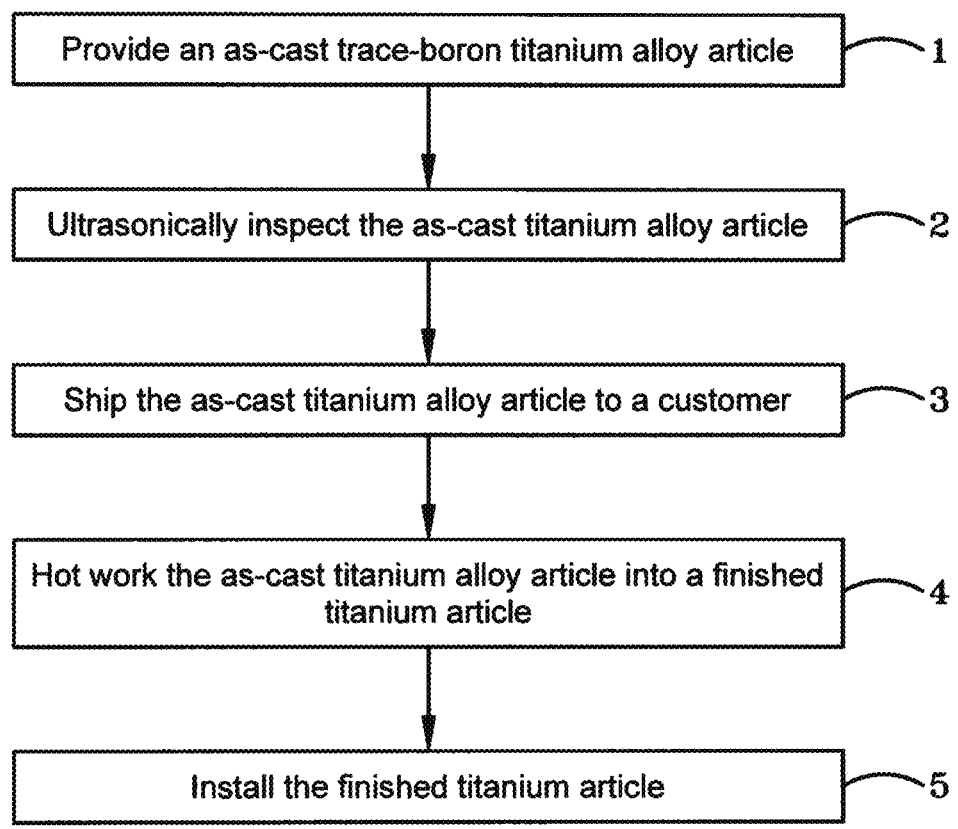
FIG. 2 is a flow chart of a sample method.

The present method allows for the ultrasonic inspectability of titanium alloy articles in the as-cast condition without recourse to significant hot working steps that are typically required. Various titanium alloys may be enhanced with addition of trace boron (B), in a range of about 0.05 or 0.10 to about 0.10, 0.15 or 0.20 percent boron by weight, to refine the grain structure as well as grain orientation in the as-cast condition, both of which minimize the interference with ultrasonic waves, and permit detection of intrinsic flaws with high confidence. The ability to inspect as-cast titanium articles with high confidence, combined with improved hot workability provided by refined grain structure, permits the manufacturing of high-quality titanium alloy articles starting with as-cast billets without the need for significant intermediate processing.

FIG. 1 compares macro grain structures in longitudinal and transverse orientations of 8-inch diameter production ingots of a workhorse titanium alloy, Ti-6Al-4V, melted using plasma arc melting in an inert gas atmosphere in a plasma arc furnace. The as-cast grains in conventional Ti-6Al-4V ingot, as expected, are extremely coarse and follow a macroscopic pattern resulting from the solidification rate. In contrast, the grain structure of Ti-6Al-4V enhanced with trace boron addition exhibits dramatic grain refinement by approximately an order of magnitude and a significantly finer macroscopic grain pattern.

Extremely coarse grains in as-cast Ti-6Al-4V resulted in significant noise levels in ultrasonic inspection (57-59 dB attenuation at 80% amplitude), which prevented any meaningful detection of internal flaws. The as-cast ingot material of Ti-6Al-4V enhanced with trace boron could be successfully ultrasonically inspected using the conventional wrought billet reference standard. An ultrasonic C-scan of the Ti-6Al-4V-0.1 B as-cast ingot was performed with an attenuation of 12-16 dB at 80% amplitude, which is an equal or better response than the wrought billet reference standard. The cast ingots of Ti-6Al-4V enhanced with trace boron were also inspected using X-ray technique, and confirmed to be free of voids, thus validating the ultrasonic inspection results.

Coarse columnar grains and colony structures are formed during cooling a conventional titanium alloy from a high temperature as beta Ti transforms to alpha Ti. There is a crystallographic relation between the alpha Ti and the parent beta Ti grain. If there is uniform nucleation of alpha Ti throughout the grain, neighboring alpha Ti particles have different crystallographic orientations, and each behave as distinct acoustic scattering entities. However, if there are only a few sites of alpha Ti nucleation within the beta Ti grain, then the alpha Ti particles in a given area all grow with the same crystallographic orientation, and a colony structure results. This colony becomes the acoustic entity. Since a colony is formed within alpha Ti grain, the colony size will be no larger than the beta Ti grain size. The size of beta Ti grains and the nature of alpha Ti particles in colony structures are important variables that influence ultrasonic noise and ultrasonic inspection in single phase and two-phase titanium alloys and materials. Therefore, the size of beta Ti grains and the nature of alpha Ti particles in colony structures may influence ultrasonic inspection results by creating undesirable noise during ultrasonic inspection. Trace boron addition to conventional titanium alloys produces dramatic refinement of beta Ti grains and also influences orientation of alpha Ti particles, both of which make the material ultrasonically inspectable with low noise levels.

Billets machined from the as-cast ingots that were successfully inspected using ultrasonic inspection could be successfully directly extruded into structural shapes. Tensile properties exhibited by extruded products are presented in Table 1. Properties of extrusions made out of as-cast ingot billets met the minimum property requirements of extrusions made out of conventional wrought billets. Prior art as-cast titanium ingots without the trace boron enhancement, on the other hand, exhibited significant defects and dimensional issues due to poor hot workability. Refined grain structure in trace boron enhanced titanium as-cast ingots imparts good hot workability whereby these as-cast ingots can be used as input stock for making products without recourse to expensive and time consuming hot working steps for refining the grain structure.

TABLE 1

Room temperature tensile properties of extrusions of Ti—6Al—4V with trace boron made directly using as-cast input stock.

| Extrusion Cross-section Shape | Tensile Strength (ksi) | Yield Strength at 0.2% Offset (ksi) | Tensile Elongation in 4D, % | Reduction of Area, % |
|---|---|---|---|---|
| π | 143 | 129 | 17 | 34 |
| π | 146 | 133 | 19 | 39 |
| ⌐¬ | 146 | 133 | 17 | 31 |
| AMS 4935 minimum | 130 | 120 | 10 | 20 |

The present invention is applicable to various titanium base alloys, such as, but not limited to, at least one of CP-Ti (Commercial Purity titanium), Ti-64 (Ti-6Al-4V), Ti-17 (Ti-5Al-2Sn-2Zr-4Mo-4Cr), Ti-6242 (Ti-6Al-2Sn-4Zr-2Mo), Ti-6242S (Ti-6Al-2Sn-4Zr-2Mo-0.1Si), Ti-10-2-3 (Ti-10V-2Fe-3Al), Ti-6246 (Ti-6Al-2Sn-4Zr-6Mo), Ti-5-2.5 (Ti-5Al-2.5Sn), Ti-3-2.5 (Ti-3Al-2.5V), Ti-6-4 ELI (Ti-6Al-4V Extra Low Interstitial), Ti-662 (Ti-6Al-6V-2Sn), Beta 21S (Ti-15Mo-2.7Nb-3Al-0.2Si), Beta C (Ti-3Al-8V-6Cr-4Mo-4Zr) and Ti-5553 (Ti-5Al-5V-5Mo-3Cr). The invention is applicable to inspection of as-cast titanium articles using ultrasonic waves to detect defects. The invention enables direct hot working of non-destructively inspected as-cast titanium input materials using processes such as forging, rolling, and extrusion into finished titanium articles.

Referring to the flow chart of FIG. 2, a method of the invention may include providing an as-cast trace-boron titanium alloy article (block 1), ultrasonically inspecting the as-cast titanium alloy article (block 2), shipping the as-cast titanium alloy article to a customer (block 3), hot working the as-cast titanium alloy article into a finished titanium alloy article (block 4) and installing the finished titanium alloy article (block 5).

The step of providing an as-cast trace-boron titanium alloy article typically includes casting the trace-boron titanium alloy article or ingot at a business location to produce the as-cast ingot or article. Although various casting methods may be used, casting the ingot may be achieved in a plasma arc furnace and may include continuous casting of the ingot, which may be cut into pieces or articles of desired length. The ingots may be formed of virtually any titanium alloy with the trace boron in weight percentages discussed above, including the titanium base alloys noted above, to provide, for example, an as-cast trace-boron titanium alloy of one of CP-Ti-0.05-0.20B, Ti-6Al-4V-0.05-0.20B, Ti-5Al-2Sn-2Zr-4Mo-4Cr-0.05-0.20B, Ti-6Al-2Sn-4Zr-2Mo-0.05-0.20B, Ti-6Al-2Sn-4Zr-2Mo-0.1Si-0.05-0.20B, Ti-10V-2Fe-3Al-0.05-0.20B, Ti-6Al-2Sn-4Zr-6Mo-0.05-0.20B, Ti-5Al-2.5Sn-0.05-0.20B, Ti-3Al-2.5V-0.05-0.20B, Ti-6Al-4V-0.05-0.20B Extra Low Interstitial, Ti-6Al-6V-2Sn-0.05-0.20B, Ti-15Mo-2.7Nb-3Al-0.2Si-0.05-0.20B, Ti-3Al-8V-6Cr-4Mo-4Zr-0.05-0.20B and Ti-5Al-5V-5Mo-3Cr-0.05-0.20B. As noted further above, the weight percent of boron in these alloys may be in the range of 0.05 to 0.10, 0.15 or 0.20.

The step of ultrasonically inspecting the as-cast titanium alloy article typically occurs after casting or providing the ingot or article and before any processing such as hot working of the ingot/article. The ingot may be cut to remove portions thereof, but typically no hot working (such as forging, rolling or extrusion) need be performed before the ultrasonic inspection. The ultrasonic inspection typically occurs at the business location and may result in a passed inspection and in a non-destructively inspected as-cast titanium alloy article, which may then be shipped from the business location to a customer remote from the business location. The non-destructively inspected as-cast titanium alloy article may then be subjected to hot working (such as forging, rolling or extrusion) to produce a finished titanium alloy article. The inspected as-cast titanium alloy article need not be shipped prior to hot working, which may be done at the business location as well if desired. Thus, a non-destructively inspected as-cast titanium alloy article may be subjected to hot working at the business location to produce a processed or hot-worked titanium alloy article (which may be a finished titanium alloy article), and for example, then be shipped to a remote location to a customer.

The hot-worked (finished) titanium alloy article may then be installed on or assembled with other components, if necessary, to form a manufactured product which includes the article. For example, the titanium alloy article may be a rotating part in a rotary engine, which may be an aircraft engine, whereby the titanium alloy rotating part is installed on or assembly with other components of the engine to produce the manufactured product in the form of the engine. The article may be configured as an aircraft part, for example, an aircraft engine part such as a nacelle, an engine casing, a rotary compressor blade, a stator airfoil or vane, a combustion chamber, a rotary turbine blade, an exhaust nozzle, an exhaust plug, or an aircraft structural or frame part such as an aircraft pylon part, an aircraft heat shield part or an aircraft fastener. The finished titanium alloy articles may also be used in the energy industry, such as oil drilling components. By way of non-limiting examples, such components may include drill pipe, pipe casing, oil pipes or tubing; offshore piping and sub-sea flowlines; offshore production, export, and re-injection risers and components; oil country tubular goods (OCTG) production tubulars and well casing and liners; offshore deepwater landing strings; offshore well-workover strings; offshore/marine fasteners and structural components; wellhead components; well jewelry or a well jewelry component (packers, safety valves, polished bore receptacles); well logging components and downhole tools; and marine submersible components, such as for remote operated underwater vehicles (ROVs). The finished articles may also include weaponry components for military or other use, such as gun barrels and armor such as used for penetration protection on tanks or other military vehicles.

The method thus allows for the production of a titanium alloy article used in a manufactured product often destined for high performance applications, such as those noted above, without the necessity for the customer or installer of the article having to ultrasonically inspect the article after hot working or other processing subsequent to the original ultrasonic inspection performed on the as-cast ingot or article. The method thus allows for the delivery of an ultrasonically inspected and warranted as-cast trace-boron titanium alloy article to a customer or user which is ready to be processed into a final article, thereby eliminating the need for the customer/user to invest resources and time for ultrasonic inspection equipment and training to operate such equipment.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A method comprising the steps of:
   providing an as-cast titanium article made up of a titanium base alloy and boron in a range of about 0.05 to 0.20 percent by weight; and
   ultrasonically inspecting the as-cast titanium article to determine whether the article has internal flaws.

2. The method of claim 1 wherein the boron is in a range of about 0.05 to 0.15 percent by weight.

3. The method of claim 2 wherein the boron is in a range of about 0.05 to 0.10 percent by weight.

4. The method of claim 1 wherein the boron is in a range of about 0.10 to 0.20 percent by weight.

5. The method of claim 4 wherein the boron is in a range of about 0.10 to 0.15 percent by weight.

6. The method of claim 1 wherein the titanium base alloy is one of: commercial purity titanium, Ti-6Al-4V, Ti-5Al-2Sn-2Zr-4Mo-4Cr, Ti-6Al-2Sn-4Zr-2Mo, Ti-6Al-2Sn-4Zr-2Mo-0.1Si, Ti-10V-2Fe-3Al, Ti-6Al-2Sn-4Zr-6Mo, Ti-5Al-2.5Sn, Ti-3Al-2.5V, Ti-6Al-4V extra low interstitial, Ti-6Al-6V-2Sn, Ti-15Mo-2.7Nb-3Al-0.2Si, Ti-3Al-8V-6Cr-4Mo-4Zr and Ti-5Al-5V-5Mo-3Cr.

7. The method of claim 1 wherein the step of ultrasonically inspecting results in a non-destructively inspected as-cast titanium article; and further comprising the step of hot working the non-destructively inspected as-cast titanium article into a finished titanium article.

8. The method of claim 7 wherein the step of hot working comprises at least one of forging, rolling and extruding the non-destructively inspected as-cast titanium article to produce the finished titanium article.

9. The method of claim 1 wherein the step of ultrasonically inspecting results in a non-destructively inspected as-cast titanium article without hot working the titanium article to refine grain structures of the titanium article before the step of ultrasonically inspecting.

10. The method of claim 9 wherein the step of ultrasonically inspecting results in the non-destructively inspected as-cast titanium article without forging, rolling or extruding the titanium article to refine grain structures of the titanium article before the step of ultrasonically inspecting.

11. The method of claim 1 further comprising, at a business location, the step of casting an ingot made up of the titanium base alloy and boron to produce the as-cast titanium article; wherein the step of ultrasonically inspecting occurs at the business location and results in a passed inspection; and further comprising, after the step of ultrasonically inspecting, the step of shipping the as-cast titanium article from the business location to a customer remote from the business location.

12. The method of claim 1 further comprising the step of forming a finished titanium alloy article from the as-cast titanium article.

13. The method of claim 12 further comprising the step of producing a manufactured product comprising the finished titanium alloy article without ultrasonically inspecting the finished titanium alloy article after the step of ultrasonically inspecting the as-cast titanium article and before the step of producing the manufactured product.

14. The method of claim 12 wherein the finished titanium alloy article is one of an aircraft part, an oil drilling component and a weaponry component.

15. The method of claim 14 wherein the finished titanium alloy article is one of a nacelle, an engine casing, a rotary compressor blade, a stator airfoil or vane, a combustion chamber, a rotary turbine blade, an exhaust nozzle, an exhaust plug, an aircraft pylon part, an aircraft heat shield part and an aircraft fastener.

16. The method of claim 14 wherein the finished titanium alloy article is one of a drill pipe, a pipe casing, an oil pipe, offshore piping, a sub-sea flowline, an offshore production riser component, an offshore export riser component, a re-injection riser component, an oil country tubular goods (OCTG) production tubular, an OCTG well casing, an OCTG liner, an offshore deepwater landing string, an offshore well-workover string, an offshore fastener, a wellhead component, a well jewelry component, a well logging component, a down-hole tool and a marine submersible component.

17. The method of claim 14 wherein the finished titanium alloy article is one of a gun barrel and armor of a military vehicle.

18. A method comprising the steps of:
casting a titanium ingot made up of a titanium base alloy and boron in a range of about 0.05 to 0.20 percent by weight; and
ultrasonically inspecting the titanium ingot to determine whether the article has internal flaws before subjecting the ingot to any hot working.

19. The method of claim 18 wherein the step of ultrasonically inspecting comprises ultrasonically inspecting the titanium ingot to determine whether the article has internal flaws before subjecting the ingot to any forging, rolling or extrusion.

\* \* \* \* \*